United States Patent [19]

Renfrew

[11] Patent Number: 4,966,135
[45] Date of Patent: Oct. 30, 1990

[54] ORTHOPEDIC CAST COVER AND METHOD OF MANUFACTURE

[76] Inventor: R. Bruce Renfrew, 601 Barneson Ave., San Mateo, Calif. 94402

[21] Appl. No.: 262,450

[22] Filed: Oct. 25, 1988

[51] Int. Cl.$^5$ .......................... A61F 13/00; A61F 5/04; A61F 5/10; A41D 19/00

[52] U.S. Cl. .................... 128/82; 128/90 R; 128/77; 128/87 R; 2/167

[58] Field of Search ............... 128/91 R, 87 R, 88, 128/77, 82, DIG. 20, 157, 165, 878, 879; 2/22, 16, 59, 161 R, 167, 168, 159, DIG. 7; 223/111, 112; 206/438

[56] References Cited

U.S. PATENT DOCUMENTS

| | | | |
|---|---|---|---|
| 2,582,648 | 1/1952 | Mowbray | 128/DIG. 20 |
| 3,083,708 | 4/1963 | Gottfried | 128/DIG. 20 |
| 3,164,152 | 1/1965 | Nicoll | 128/87 R |
| 3,186,404 | 6/1965 | Gardner | 128/DIG. 20 |
| 3,245,405 | 4/1966 | Gardner | 128/DIG. 20 |
| 3,338,237 | 8/1967 | Sconce | 128/87 R |
| 3,351,055 | 11/1967 | Gottfried | 128/87 R |
| 3,424,151 | 1/1969 | Ericson | 128/87 R |
| 3,561,435 | 2/1971 | Nicholson | 128/87 R |
| 3,785,374 | 1/1974 | Lipson | 128/82 |
| 4,036,220 | 7/1977 | Bellasalma | 128/82 |
| 4,043,326 | 8/1977 | Little et al. | 128/82 |
| 4,139,003 | 2/1979 | Little et al. | 128/82 |
| 4,254,765 | 3/1981 | Brown et al. | 128/82 |
| 4,363,317 | 12/1982 | Broucek | 128/82 |
| 4,562,834 | 1/1986 | Bates et al. | 128/82 |
| 4,639,945 | 2/1987 | Butz | 2/22 |

Primary Examiner—Robert A. Hafer
Assistant Examiner—Michael Brown

[57] ABSTRACT

A waterproof, orthopedic cover for use over an injured limb and a method for producing the cover is disclosed. The cover is composed of polyurethane and has a receiving end through which the injured limb is inserted. A closed end is also present and designed to accommodate either a hand or a foot. The polyurethane cover is bounded by a pair of seams which render the cover tear resistant.

7 Claims, 1 Drawing Sheet

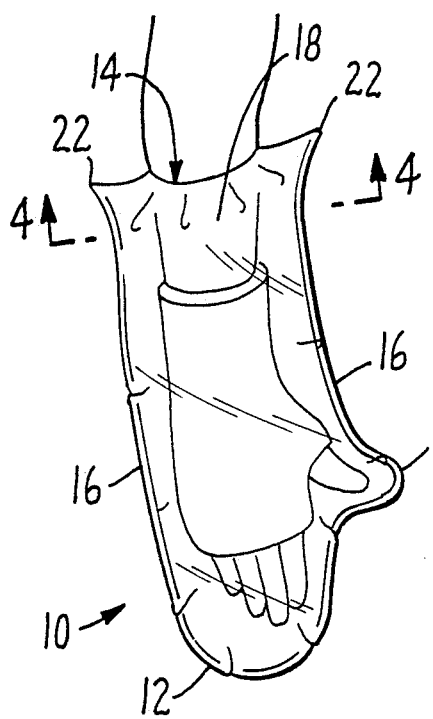
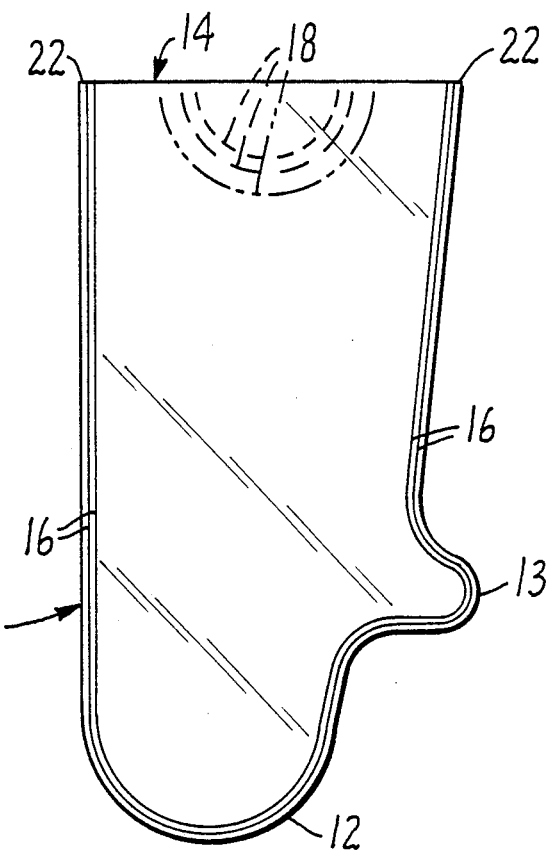
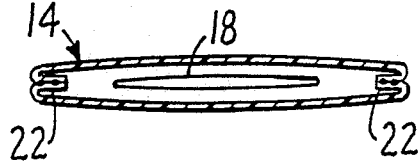
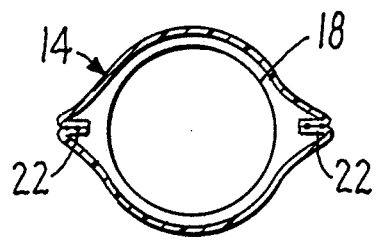
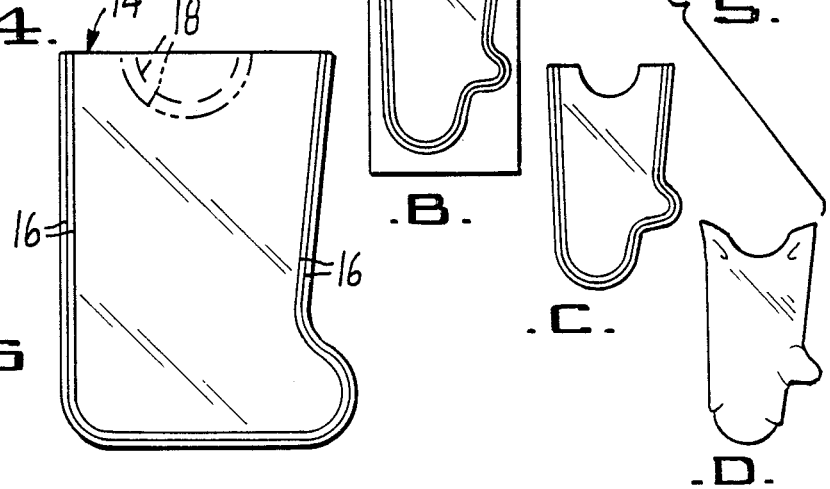

ORTHOPEDIC CAST COVER AND METHOD OF MANUFACTURE

TECHNICAL FIELD

The subject invention relates generally to protective covers and their manufacture and more specifically to a waterproof, orthopedic cover for use over an injured limb.

BACKGROUND OF THE INVENTION

Injured areas must often be protected with a cast, bandage or other protective dressing. These areas should be kept dry and free from water or other moisture. Plaster casts disintegrate when wet and even casts made from synthetic materials such as fiberglass should be kept moisture-free to prevent the cast lining from deteriorating and the skin under the cast from macerating.

Commonly used protective devices include a bag and strap variety such as disclosed in U.S. Pat. Nos. 4,562,834 and 4,363,317. These devices consist essentially of a large vinyl bag with a string or strap to secure the open end of the cover over the affected area. These covers suffer from several drawbacks. First, they are relatively difficult to put on an arm without assistance since the string or strap must be manipulated around the cast or bandage. Additionally, many of these devices are not truly watertight and cannot be completely submersed. Further, the material from which these bags are constructed is subject to tearing when in contact with rough fiberglass cast edges, thus rendering the coverings useless.

Another commonly used cast protector consists of a thin latex bag as described in U.S. Pat. Nos. 4,043,326 and 4,139,003. These bags tear easily, failing to last the full convalescence period. Additionally, these devices may fit improperly and can be so tight that blood flow is restricted or so loose that they leak.

Another protective device consists of a vinyl bag with a flat latex diaphragm and collar as described in U.S. Pat. No. 4,639,945. Although generally more effective than the bags disclosed above, the vinyl used is susceptible to tears. The diaphragm must be cut to size for most patients, a practice to which some patients and orthopaedic technologists object.

The present invention overcomes the above-noted shortcomings of conventional protective coverings. The covering can be applied easily one-handed, without assistance. The material used is durable, flexible and provides an effective watertight seal. Thus, the covered limb can be completely submersed and still maintain a waterproof environment within the protective cover. These and other advantages of the subject invention will become apparent to those skilled in the art upon a reading of the Description of the Preferred Embodiment together with the drawings.

SUMMARY OF THE DISCLOSURE

A waterproof, orthopedic cover for use over an injured limb and a method for making the cover is disclosed. The cover comprises a polyurethane enclosure that includes a receiving end defining an opening through which an injured limb is inserted. The opening is configured to form a watertight seal around the limb and over a cast or other protective dressing.

The enclosure includes a closed end that is either mitten or sock-shaped to fit over a hand or foot, respectively.

The cover is manufactured by folding a polyurethane sheet in half resulting in three open edges and a folded end. The three open edges are sealed to form an enclosure; a hole is cut into the folded end; and the enclosure is turned inside out.

The enclosure of this invention as made by the method of this invention is folded at the receiving end where the opening is located and includes at least one seam surrounding the remainder of the enclosure. This enclosure can also include pull tabs at the sides of the receiving end.

BRIEF DESCRIPTION OF THE DRAWINGS

FIG. 1 is a perspective view of the subject invention showing its use over an injured arm.

FIG. 2 is a side view of the subject invention before it is turned inside out for use.

FIG. 3 is a sectional view showing an opening through which an injured limb is inserted into the instant invention.

FIG. 4 is a cross-sectional view of the present invention taken along lines 4—4 of FIG. 1, showing the opening as it appears when stretched to accommodate the injured limb.

FIGS. 5A through 5D show the manufacturing sequence of the subject invention.

FIG. 6 is a side view of the present invention for use over an injured foot.

DESCRIPTION OF THE PREFERRED EMBODIMENT

Referring now to FIGS. 1 and 2, a protective limb cover according to the present invention can be seen. Limb cover 10 is an enclosure with a closed end 12 and receiving end 14. Limb cover 10 also includes at least one and preferably two seams 16 running substantially around the closed end 12 to receiving end 14.

As best illustrated in FIGS. 3 and 4, receiving end 14 defines an opening 18, for receiving an injured limb. The term limb as used herein refers to an arm, leg, forearm or lower leg which might be protected by a bandage, cast or other dressing. Opening 18 has a diameter less than the diameter of receiving end 14 and the limb to be protected. In this way, limb cover 10 can fit snugly over the injured area and maintain a watertight seal between the injured limb and the external environment. Preferable diameters of the opening 18 range from 1 inch to 5 inches, depending on the age of the patient and the circumferences of the limb proximal to the injured area. For instance, a limb cover to fit over an average casted adult arm would have an opening 18 with a diameter of approximately 2 to 2½ inches.

As illustrated in FIGS. 2 and 6, closed end 12 can be mitten-shaped with a thumb compartment 13 for use over an injured arm or sock-shaped for use over an injured leg. In this way, a patient's hand or foot can fit comfortably within the enclosure.

The seams 16 resist tears that might occur due to sharp and bulky casts. This problem more often occurs in the prior art when a large foot cast comes in pressure contact with the protective cover.

Seams 16 can be formed using radio frequency (RF) heating to seal the closed end 12. An RF sealer, such as a 10 kilowatt unit, is employed in the present invention. The sealer applies a current to a brass die, in the desired shape of a mitten or sock, that transfers heat to the limb cover undergoing manufacture. Sealing time takes 2-4 seconds.

As best illustrated in FIGS. 1-4, adjacent to and continuous with seams 16 are tabs 22 to aid in pulling the limb cover 10 over the injured area. Tabs 22 are peak-shaped and formed by the intact portion of the receiving end 14 that borders on the seams 16. Tabs 22 will be discussed in greater detail below.

Limb cover 10 is composed of heavy-gauge film polyurethane which combines durability and elasticity. Film polyurethane can stretch to five times its length and return to within 3% of its original length. Thus, opening 18 of limb cover 10 can be stretched over the protective dressing and return to its original size to fit snugly around the limb to be protected. Film thickness ranges from 0.005 to 0.020 inches and preferably 0.005 to 0.010 inches thick are utilized.

Limb cover 10 can be fabricated using single piece construction in the following manner. The polyurethane film is cut to a length more than two times the length of the completed limb cover. The film is then folded over with a fold 13 at the receiving end 14 forming a front side 15a and a back side 15b (FIG. 5A in which the ultimate outline of the sealed periphery is shown in phantom). A mitten or sock-shaped, RF heated brass die is pressed against the folded film to make the seal 16 between the front and back sides 15a and 15b from two spaced apart positions along the fold 13 (FIG. 5B). Seal time takes approximately 2-4 seconds.

Next, opening 18 is formed by punching a semi-circular hole across the fold 13 at the folded receiving end 14 using a die-type punch. This produces a circular opening when limb cover 10 is in use (FIG. 5C). The size of the opening can be varied to accommodate different limb sizes. The excess polyurethane film is then trimmed from around seams 16. (FIG. 5C) and the limb cover is turned inside out (FIG. 5D). Air pressure can be used to uniformly turn limb cover 10 inside out, as well as assure that no hole or weak seam is present through which water might leak while the limb cover is in use.

When limb cover 10 is turned inside out, seams 16 are positioned in the interior of the limb cover 10 (FIG. 5D). This not only serves an aesthetic purpose, but also helps to hold the sides of the enclosure apart thereby functioning to ease insertion of an injured limb into opening 18. Further, as illustrated in FIGS. 3 and 4, when limb cover 10 is turned inside out, the corners of the remaining fold in the receiving end form peaks 22 that function as handles to aid in pulling the limb cover 10 over the injured appendage. When limb cover 10 is pulled over the limb to be protected, opening 18 enlarges to accommodate the extra width imposed by the cast or dressing. Limb cover 10 is placed completely over the cast and opening 18 shrinks back to its original diameter to snugly hug the injured limb.

Thus a watertight, protective covering for use with a cast, bandage or other dressing is disclosed. Although a preferred embodiment of the subject invention has been described in some detail, it is understood that obvious variations can be made without departing from the spirit and scope of the invention as defined by the appended claims.

What is claimed is:

1. A watertight, protective limb cover comprising an elongate, integral polyurethane film enclosure for receiving the limb to be protected, said enclosure having a front side and a back side, said front and back sides connected together to form a closed end and a receiving end, said receiving end formed from a single polyurethane film fold connecting said front and back sides of said enclosure and adapted to have an opening created along said fold with a diameter smaller than the diameter of the receiving end and configured to form a watertight seal between the limb to be protected and the external environment, said closed end formed by a continuous seal between the polyurethane forming said front and back sides.

2. The protective limb cover of claim 1 wherein said closed end is completely bounded by at least one continuous seam to resist tearing of said enclosure.

3. The protective limb cover of claim 2 wherein said at least one seam comprises a pair of adjacent seams.

4. The limb cover of claim 1 including a pair of pulling tabs formed where said closed end and said receiving end meet.

5. A watertight protective limb cover comprising an elongate, integral, polyurethane film enclosure having a closed end and an open end for receiving the limb to be protected, said enclosure formed from an at least double length of polyurethane film folded over onto itself with one length of said double length of film forming a front side of the enclosure and the other length of said double length of film forming the back side of the enclosure and with the fold forming the receiving end of the enclosure, at least one continuous sealed seam between the double length of film and extending from said fold adjacent the opposite ends thereof along the opposite edges of the film length and around the length of the film remote from said fold, said continuous seam bounding said closed end of said closure, said receiving end having an opening through said fold to receive the limb to be protected and to form a watertight seal between the closure and the limb to be protected.

6. The protective limb cover of claim 5 including a second continuous sealed seam adjacent said one continuous sealed seam.

7. A watertight protective limb cover comprising an elongate, integral, polyurethane film enclosure having a closed end and an open end for receiving the limb to be protected, said enclosure formed from an at least double length of polyurethane film folded over onto itself with one length of said double length of film forming a front side of the enclosure and the other length of said double length of film forming the back side of the enclosure and with the fold forming the receiving end of the enclosure, a pair of adjacent continuous sealed seams between the double length of film and extending from said fold adjacent the opposite ends thereof along the opposite edges of the film length and around the length of the film remote from said fold, said continuous seams bounding said closed end of said closure, said receiving end having an opening through said fold to receive the limb to be protected and to form a watertight seal between the closure and the limb to be protected, the portion of said double length of polyurethane film between said sealed seams and the adjacent edges of the film length contained within said enclosure.

* * * * *